United States Patent [19]
Krell

[11] Patent Number: 5,572,315
[45] Date of Patent: Nov. 5, 1996

[54] OPTICAL SENSOR SYSTEM

[75] Inventor: Stephan Krell, Schwabach, Germany

[73] Assignee: Temic Telefunken microelectronic GmbH, Heilbronn, Germany

[21] Appl. No.: 339,720

[22] Filed: Nov. 14, 1994

[30] Foreign Application Priority Data

Nov. 30, 1993 [DE] Germany .................. 43 40 681.5

[51] Int. Cl.⁶ ............................................. G01N 21/17
[52] U.S. Cl. ........................................ 356/136; 318/DIG. 2
[58] Field of Search ......................... 356/136; 318/483, 318/444, DIG. 2; 250/341.8

[56] References Cited

U.S. PATENT DOCUMENTS

| | | | |
|---|---|---|---|
| 5,323,637 | 6/1994 | Bendicks et al. | 318/483 |
| 5,391,891 | 2/1995 | Wiegleb et al. | 250/341.8 |

FOREIGN PATENT DOCUMENTS

| | | |
|---|---|---|
| 0043522 | 1/1982 | European Pat. Off. . |
| 2420594 | 6/1975 | Germany . |
| 3243372 | 5/1984 | Germany . |
| 3314770 | 10/1984 | Germany . |
| 3823300 | 8/1989 | Germany . |
| 3806881 | 9/1989 | Germany . |
| 4006174 | 7/1991 | Germany . |
| 4019066 | 12/1991 | Germany . |
| 4202121 | 12/1992 | Germany . |
| 4142146 | 6/1993 | Germany . |

*Primary Examiner*—Richard A. Rosenberger
*Attorney, Agent, or Firm*—Spencer & Frank

[57] ABSTRACT

A sensor system for the measurement of the optical conditions at a boundary surface between a first medium that is a solid body and a second medium whose refracting indices are different. The sensor system has an optical unit comprising at least one sending unit with at least one sending element, at least one receiving unit with at least one receiving element, and an optical path connecting the send unit(s) to the receiving unit(s). A light-conducting body with a base surface and two optically active end surfaces is arranged in the optical path, where the base surface of the light-conducting body is attached to the surface side of the first medium between the sending unit(s) and the boundary surface. The first end surface of the light-conducting body is directed towards the sending unit(s) and the second end surface of the light-conducting body is directed towards the receiving unit(s). The two end surfaces of the light-conducting body, the light emission surface of the sending unit(s) and the light admission surface of the receiving unit(s) are made with a predetermined convex shape.

5 Claims, 1 Drawing Sheet

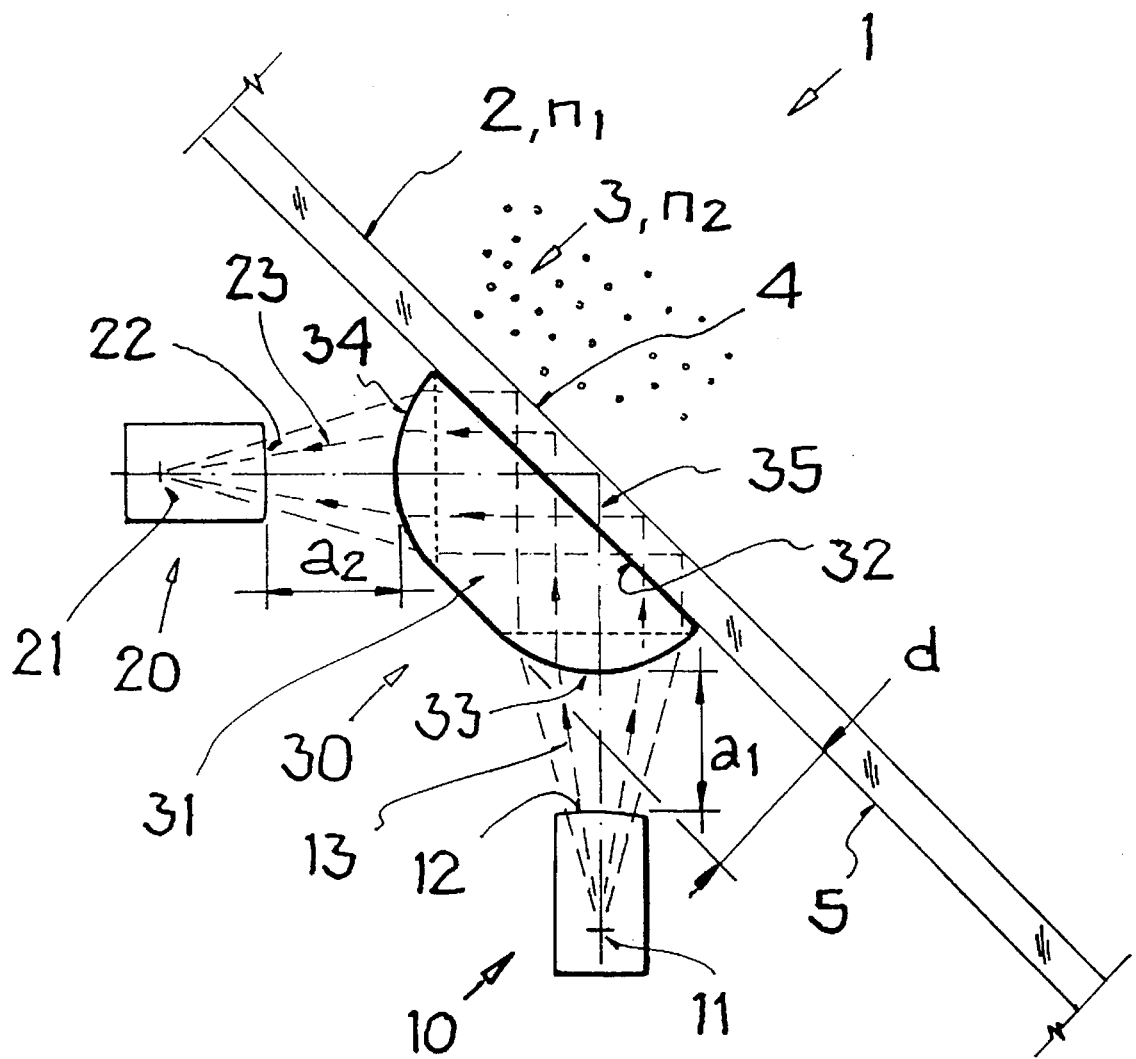

OPTICAL SENSOR SYSTEM

BACKGROUND OF THE INVENTION

The optical unit of optical sensor systems consists of at least one sending unit with one or several sending elements, at least one receiving unit with one or several receiving elements and an optical path through which the sending unit(s) and receiving unit(s) are coupled. To determine the optical relationships at a boundary surface—which separates two media with different refractive indices from one another—the beam sent from the sending element(s) is reflected once or more than once at this boundary layer, the reflected beam is detected by the receiving element(s), and the detected beam is processed further as a received signal in an evaluation unit of the sensor system. If the optical relationships change at the boundary surface, this leads to a variation in the received signal that can be evaluated by the evaluation unit. For instance, motor vehicle rain sensors evaluate the changes in optical relationships caused by wetting of the outside of the windscreen (front or rear window): a part of the beam sent out from the sending unit is decoupled from the window by the moisture and therefore can no longer reach the receiving unit. This signal loss is registered and evaluated; it is possible for the windscreen wiper to be operated at this stage.

To avoid a further reduction in visibility for the driver, the optical unit must be made as compact as possible. In order to be able to reliably acquire changes to the optical properties, the sensitivity over the entire sensitive surface of the optical unit must be uniform and adequate (i.e., the illumination must be as homogeneous as possible). However, these two conditions cannot be satisfied with only two optically active surfaces (lens surface) so that either multiple reflections of the beam must be effected at the boundary surface or sensor systems with a complicated optical system are used. However, this suffers from the disadvantages that, firstly, the beam must be transmitted over a long path within a medium, resulting in small received signals owing to the high degree of absorption (which depends on the particular medium) and that, secondly, it frequently occurs that only part of the beam from the sending unit(s) enters the medium so that the signal change to be evaluated is small and dependent on the medium.

SUMMARY OF THE INVENTION

The object of the invention is to provide an optical unit of a sensor system with simple optics and small size where the disadvantages mentioned above are avoided and having the advantageous properties, in particular good sensitivity and homogeneous sensitivity distribution.

The above object is generally achieved according to the invention in that in order to ensure homogeneous sensitivity distribution for a small-sized optical unit, the unit has four optically active surfaces (refraction/reflection surfaces) which are arranged between the sending element(s) of the sending unit(s) and the receiving element(s) of the receiving unit(s): two optically refractive surfaces are formed by the two outwardly curved (convex) end surfaces of a light-conducting body placed in the optical path, the base surface of this body being affixed (for instance with the help of a transparent adhesive) to the surface side of the first medium (a solid-state device) facing the sending unit(s) and receiving unit(s). Furthermore, the end surface (beam emission surface/beam admission surface) of the housing of sending unit(s) and receiving unit(s) is also made in an outwardly curved (convex) form so that they act as two further optically refractive surfaces (convex lens). The beam emission surface of the sending unit and the beam admission surface of the receiving unit each have a slightly convex shape while the two end surfaces of the light-conducting body are of relatively greater convex shape. To ensure a symmetrical beam path and thus a size as compact as possible, both beam emission surface and beam admission surface have the same curved shape as do the two end surfaces of the light-conducting body.

The light-conducting body—which can, for example, be made of a plastic material and be an integrated unit in the form of a prismatic basic body with two convex lenses as end surfaces—serves two purposes: firstly, it serves as a "collecting lens" in front of sending unit(s) and receiving unit(s) and, together with the specially shaped beam admission surface and beam emission surface of the receiving unit(s) and sending unit(s) respectively, allows a compact design; secondly, it serves to couple the beam into the first medium and to decouple the light from this medium and thus ensures good sensitivity of the optical unit.

The optical unit of the sensor system incorporates numerous advantages:

- it is of simple and thus low-cost design;
- it is of compact construction and thus has a small size; the distance between sending unit(s) and receiving unit(s) and the light-conducting body can thus be kept very small;
- owing to the single reflection of the beam at the boundary surface, the beam travels over only a small path in the first medium between sending unit(s) and boundary surface, so that no problems arise as a result of beam absorption;
- by coupling the beam into the boundary surface using the light-conducting body, the sensitivity is high and;
- any kind of electromagnetic beam can be used—particularly visible light or IR radiation.

BRIEF DESCRIPTION OF THE DRAWING

The invention will now be described below with the help of an embodiment example shown in the Figure which shows the optical unit according to the invention of an optical sensor system that functions as a rain detector and that is fitted to the windscreen in motor vehicles and operates with IR radiation.

DETAILED DESCRIPTION OF THE PREFERRED EMBODIMENT

As the Figure shows, the optical unit 1 of the sensor system has a sending unit 10 with the sending element 11 (sending diode); and a receiving unit 20 with the receiving element 21 (receiving diode); the housing of the sending unit 10 and 06 the receiving unit 20 each is, for example, made in the form of a transparent plastic housing. In the optical path 30 between sending unit 10 and receiving unit 20, there is a light-conducting body 31 (base surface 32, face surfaces 33, 34) made, for example, of plexiglass that serves to inject the IR beam 13 emitted from the sending element 11 into the windscreen 2 and to decouple the beam 35 injected into the windscreen 2 and the IR beam 23 reflected at the boundary surface 4 between windscreen 2 (refracting index $n_1$) and outer side (air) 3 (refracting index $n_2$). The base surface 32 of the light-conducting body 31 is affixed directly (without air gap) to the inside 5 of the windscreen 2 by means of a transparent adhesive. The two end surfaces 33 and 34 are oriented into of the body 31 the beam path of the emitted beam 13 and the reflected beam 23, respectively. The light emission surface 12 (end surface) of the sending unit 10 and the light admission surface 22 (end surface) of the receiving unit 20—the first two optically active surfaces—have a preset slightly convex shape (obtained, for instance, by a polynomial of the tenth degree); the two end surfaces 33, 34 of the light-conducting body 31 as further optically active surfaces have a preset strongly convex shape (obtained, for instance, by another polynomial of the tenth degree). By the interaction on the one hand of the arrangement of the optically active surfaces and on the other hand their specially curved shape, the beam 13 emitted from the sending element 11 of the sending unit 10 can be bundled—without major reflection losses at the boundary surfaces—in the receiving element 21 of the receiving unit 20.

If the outside 3 of the windscreen 2 becomes wet by raindrops, part of the beam 35 coupled into the windscreen 2 is decoupled from it and thus does not reach the receiving element 21; this can be registered and processed by an evaluation unit connected in series behind it. For example, the sending element 11 of the sending unit 10 is made as an IR sending diode and the receiving element 21 of the receiving unit 20 as an IR receiving diode. The light-conducting body 31 is made, for example, of plexiglass and has an elliptical base surface with a major semi-axis of 45 mm and a minor semi-axis of 25 mm; its thickness d is, for instance, 17 min. The distance $a_1$ between the first end surface 33 of the light-conducting body 31 and the light emission surface 12 of the sending unit 10 and the distance $a_2$ between the second end surface 34 of the light-conducting body 31 and the light admission surface 22 of the receiving unit 20 is, for instance, 15 mm in each case. If there is only slight wetting of the windscreen, the windscreen wiper is actuated if the received signal varies by, for instance 5% (by way of comparison: wetting of the outside of the windscreen 2 by heavy rain leads, for instance, to a 20% change in the received signal).

What is claimed is:

1. A sensor system for determining the optical conditions at a boundary surface which separates a first medium in the form of a solid body and a second medium whose refracting indices ($n_1$, $n_2$) are different from one another, with the sensor system having an optical unit which comprises:

at least one sending unit with at least one sending element and having a light emission surface;

at least one receiving unit with at least one receiving element, and having a light admission surface;

an optical path linking the sending unit with the at least receiving unit;

a light-conducting body arranged in the optical path and having a base surface and first and second optically active end surfaces, with the base surface of the light-conducting body being affixed to the surface side of the first medium disposed between the at least one sending unit and the at least one receiving unit and the boundary surface, and with the first end surface of the light-conducting body facing the light emission surface of the at least one sending unit and the second end surface of the light-conducting body facing the light admission surface of the receiving unit;

and wherein the first and second end surfaces of the light-conducting body, the light emission surface of the at least one sending unit, and the light admission surface of the at least one receiving unit are each provided with a predetermined convex shape, with the light emission surface of the sending unit and the light admission surface of the receiving unit each having such a weakly convex shape and with the two end surfaces of the light-conducting body each having such a strongly convex shape that the emitted radiation received on the base surface of the light-conducting body is distributed homogeneously and the distance ($a_1$) between the at least one sending unit and light-conducting body and the distance ($a_2$) between the at least one receiving unit and light-conducting body are minimal.

2. Sensor system in accordance with claim 1, wherein the light emission surface of the at least one sending unit and the light admission surface of the at least one receiving unit have the same weak convex shape.

3. Sensor system in accordance with claim 2, wherein the first and second end surfaces of the light-conducting body have the same strong convex shape.

4. Sensor system in accordance with claim 1, wherein the base surface of the light-conducting body is in a planar arrangement on surface side of the first medium such that there is no air gap between the base surface of the light conducting body and the one surface side of the first medium.

5. Sensor system in accordance with claim 1, wherein the light-conducting body is attached to the one surface side of the first medium by a transparent adhesive.

* * * * *